United States Patent [19]
Shi

[11] Patent Number: 6,113,529
[45] Date of Patent: Sep. 5, 2000

[54] RADIOACTIVE SEED HANDLING DEVICE

[76] Inventor: Xiaolin Shi, 2800 Jills Trail, Edmond, Okla. 73003

[21] Appl. No.: 09/129,762

[22] Filed: Aug. 6, 1998

[51] Int. Cl.$^7$ .................................................. A61M 36/00
[52] U.S. Cl. ...................................... 600/7; 600/1
[58] Field of Search ........................................ 600/1, 7, 8

[56] References Cited

U.S. PATENT DOCUMENTS

| | | | |
|---|---|---|---|
| 1,954,868 | 4/1934 | Failla et al. ............................. | 174/177 |
| 2,009,393 | 7/1935 | Faillla .................................... | 128/217 |
| 2,269,963 | 1/1942 | Wappler ................................. | 128/217 |
| 3,224,432 | 12/1965 | Billingsley ............................. | 128/1.2 |
| 3,516,160 | 6/1970 | Leffler ................................... | 433/95 |
| 3,757,995 | 9/1973 | Armstrong ............................. | 221/211 |
| 4,241,728 | 12/1980 | Mirell ..................................... | 128/1.1 |
| 4,401,108 | 8/1983 | Galkin et al. .......................... | 128/1.1 |
| 4,561,687 | 12/1985 | Bostrom ................................ | 294/64 |
| 4,759,345 | 7/1988 | Mistry ................................... | 600/8 |
| 4,763,671 | 8/1988 | Goffinet ................................ | 600/7 |
| 5,061,145 | 10/1991 | Genis et al. ........................... | 414/325 |
| 5,147,282 | 9/1992 | Kan ........................................ | 600/1 |
| 5,242,373 | 9/1993 | Scott et al. ............................ | 600/7 |
| 5,876,384 | 2/1999 | Dragan et al. ......................... | 433/91 |
| 5,906,574 | 5/1999 | Kan ........................................ | 600/3 |

OTHER PUBLICATIONS

Standard Imaging, Iodine and Palladium Seed Handling and Needle Loading Instruments, (no date), brochure, p. 3.
Standard Imaging, Luthamann Source Positioning QA Tool for HDR and LDR Brachytherpay, (no date), brochure, 2 pages.
Standard Imaging, Autoradiographic Jig, (no date), brochure, 1 page.
NW Radiation Therapy Products, Custom Shielding 125 Iodine/ 103 Palladium Implant Horizontal Needle Box, Needle Loading Shield for 125 Iodine or 103 Palladium, Needle Loading Box, NW Needle Loading Carousel, (no date), brochure, 1 page.
Medical Radiation Devices, Inc., Needle Seed Loading/ Handling System for Prostate Seed Implants, (no date), brochure, 7 pages.
CII, (title unknown), (no date), 2 pages, excerpt from catalog p. 24 and 66.
(author unknown), Seed Hopper, (no date), brochure, 1 page.
(author unknown), Protective Shielding, Devices & Storage, (no date), 2 pages, excerpts from catalog pp. 96 and 97.
(author unknown), (title unknown), (no date), 1 page, excerpt from catalog p. 100.

*Primary Examiner*—Cary O'Connor
*Attorney, Agent, or Firm*—Robert Treece

[57] ABSTRACT

A radioactive seed handling device having a base and a needle rack removably attached to the base for holding a plurality of needles generally parallel in a single plane while radioactive seeds are dropped into the needles. The needle rack includes a front shield for shielding an operator from radiation emitted from needles in the rack. The device may also include a vacuum source and a seed handling wand connected to the vacuum source by a conduit, with the wand having a handle and a probe. The probe is connected to the handle and extends from the handle at an angle between fifteen and seventy-five degrees.

13 Claims, 4 Drawing Sheets

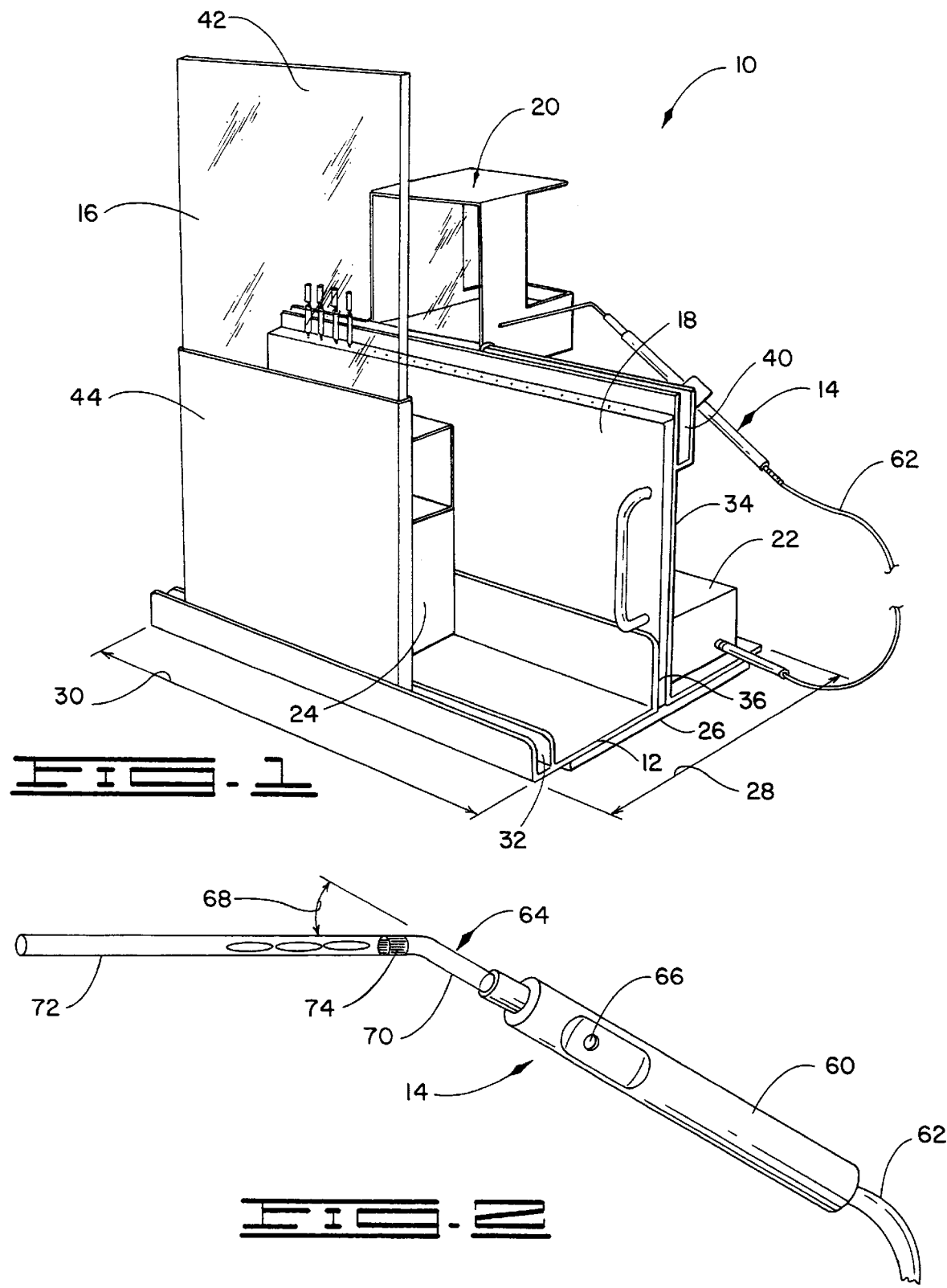

RADIOACTIVE SEED HANDLING DEVICE

BACKGROUND OF THE INVENTION

1. Field of the Invention

The present invention relates to a radioactive seed handling station for use in preparing needles containing radioactive seeds for implant in or around cancerous growths.

2. Description of the Prior Art

In the medical field of radiation oncology, small pieces of low level radioactive material known as "seeds" are placed around a cancerous growth by injection with needles. Various concentrations of seeds are injected and placed depending on the particular circumstances of the cancer. One of the methods for adjusting the placement and concentration of radioactivity is to load spacers along with the seeds into a needle before injection, thereby spacing the seeds apart after the injection and providing control over the concentration of radiation from the injection. Of course, multiple injections are commonly used and the spacing of the injections themselves also provides control over the concentration of radiation.

Before the actual injection of radioactive seeds, several procedures are completed to insure the desired dosage of radiation is applied. These procedures includes: verifying the radiation of the seeds; counting the seeds; the actual loading of spacers and seeds in a needle; and, verifying the number and placement of seeds and spacers in the needle.

Prior to the current invention, various devices were used to hold needles while they were loaded, and other devices stored loaded needles temporarily while other needles were being loaded, while other devices were used to hold the needles while the loading was confirmed. This repeated movement of the needles, along with the fact that the needles were generally loaded by using tweezers to drop seeds or spacers into the needles, provided several disadvantages, such as: increased radiation exposure to the individual responsible for loading the needles; increased chances for contamination; increased chances for the seeds and/or needles to be placed in the wrong order for insertion; and, consumption of time. In addition, the use of the various shields and devices for seed verification, needle loading and loading verification often required multiple autoclaves for sterilization, or at least multiple trips to a single autoclave, thereby tying up valuable resources. If an error was made, such as loading a seed where a spacer should be, the entire needle would need to be dumped and reloaded. Prior art devices did not provide a means to verify that a stack of seeds and spacers were in proper order before they were loaded into a needle. In general, prior to the current invention, valuable time and resources were used while unwanted exposure and the risk of contamination were large.

SUMMARY OF THE INVENTION

In view of the foregoing disadvantages inherent in the various known types of seed systems now present in the prior art, the present invention provides a radioactive seed handling station wherein the same can be utilized reliably in those situations where seed verification, needle loading and/or needle verification is desired. As such, the general purpose of the present invention, which will be described subsequently in greater detail, is to provide a new and improved radioactive seed handling station which has all the advantages of prior art devices and none of the disadvantages.

To attain this, the present invention essentially comprises a compact work station for handling radioactive seeds. The station includes multiple shields, a vacuum-powered seed handling catheter, various seed or spacer holding devices, and a removable needle holder which may be used to directly verify the loaded needles by autoradiographic means.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in this application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved radioactive seed handling device which may be easily and efficiently manufactured and marketed.

It is a further object of the present invention to provide a new and improved seed handling device which is of compact size to facilitate sterilization.

An even further object of the present invention is to provide a new and improved seed handling device which provides enhanced protection for an operator working with radioactive seeds.

Another object of the present invention is to provide a new and improved seed handling device which decreases the time required to prepare, load and verify the loading of seeds and spacers in a needle.

Yet another object of the present invention is to provide a new and improved seed handling device which provides easy verification through autoradiographic means.

Even another object of the present invention is to provide a new and improved seed handling device which allows visual verification of seeds and spacers prior to loading into a needle.

Still another object of the present invention is to provide a new and improved seed handling device which provides some of the advantages of the prior art, while simultaneously overcoming some of the disadvantages normally associated therewith.

These, together with other objects of the invention, and along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a front perspective view of a radioactive seed handling device constructed in accordance with the present invention.

FIG. 2 is a view of a seed handling wand of the invention of FIG. 1.

DETAILED DESCRIPTION OF THE PREFERRED EMBODIMENTS

Figure 3:
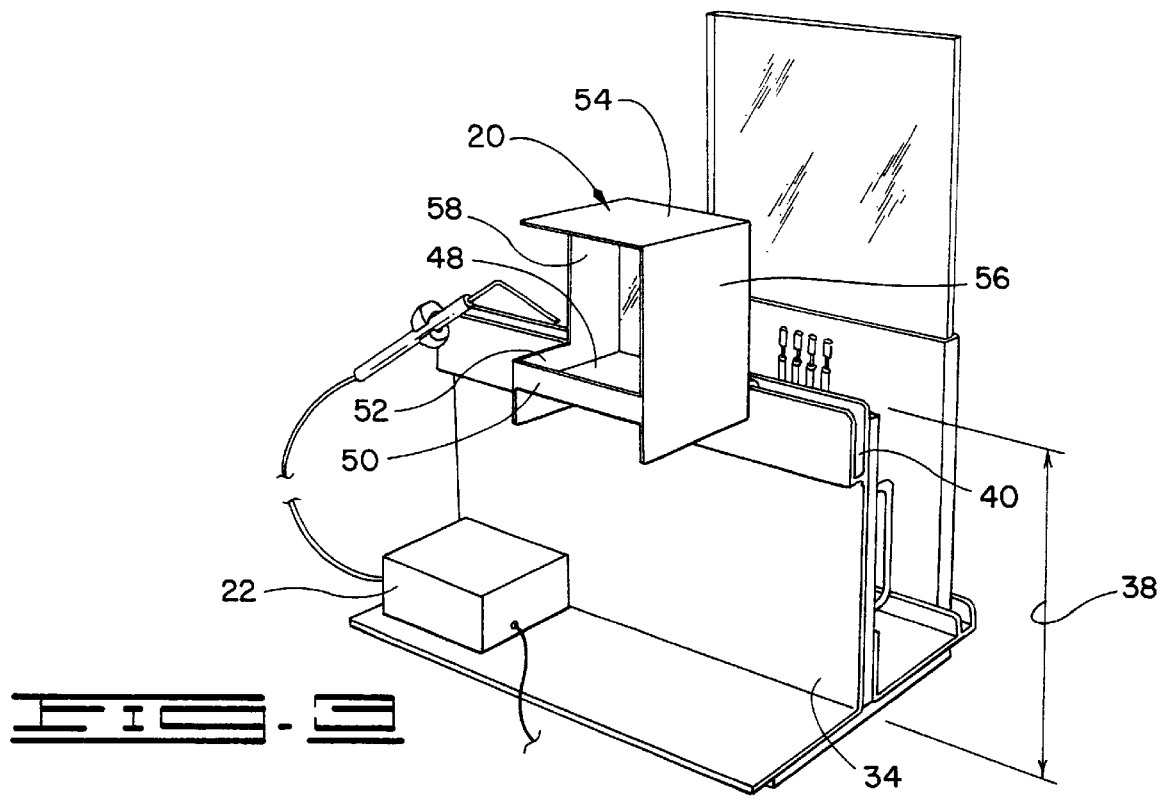
FIG. 3 is a rear perspective view of a radioactive seed handling device constructed in accordance with the present invention.

Referring to the drawings in detail and to FIG. 1 in particular, reference character 10 generally designates a radioactive seed handling device constructed in accordance with the present invention.

The seed handling device has a base 12, a vacuum-powered seed handling wand 14, a front shield 16, needle rack 18, and shielded seed working tray 20. The device 10 may also include a vacuum source 22, and a bulk seed storage container 24.

The base 12 has a bottom 26, which provides the base 12 with an overall width 28 and an overall length 30. Preferably the width 28 and the length 30 are such that the base will fit inside a standard-sized autoclave for sterilization. Means is provided on the front of the base 12 for the attachment of front shield 16. While the front shield 16 may be solidly attached, or even slidingly attached, preferably the shield is removably attached, such as by groove 32. The base 12 should also include means for holding the needle rack 18 as well as the shielded seed working tray 20. One way to accomplish this it to provide center divider 34 and groove 36. In this way, the needle tray may be held between the groove 36 and the divider 34 provides a location for mounting the seed working tray 20.

The base 12 may be made from a single piece and molded to the proper shape, but it has been found that one easy way to make the base is to securely fasten together multiple pieces. The base 12 may be made from any durable material which can withstand the temperatures required for sterilization in an autoclave. Preferably the base is a metallic material such as stainless steel with its various pieces welded together to form grooves 36 and 32, as well as center divider 34.

The center divider 34 preferably has a height 38 (FIG. 3) which will allow the base to fit inside a standard autoclave. At or near the top of the center divider 34 should be means for attaching the shielded seed working tray 20. One suitable means which will allow the working tray 20 to be moved to various locations along the center divider 34 is groove 40. In this way a lip on the seed working tray 20 can hook in the groove 40 and allow the operator to slide the working tray anywhere along the groove 40. This will allow the operator to select a comfortable shielded position to work.

The front shield 16 is preferably connected to the front of the base 12. More preferably, the shield 16 is movably connected and most preferably the shield is movably and removably connected to the base 12. At least a portion 42 of the front shield 16 is transparent. This allows the operator to remain in a shielded area and still have a view of the seeds while working. In the preferred embodiment, the lower portion 44 of the shield 16 is made from a non-transparent material such as stainless steel. This is simply a function of economy and the entire shield may be transparent. In addition, by making the lower portion of the shield solid, the shield is not likely to be placed in the groove 32 upside down which could mark or scratch the transparent material.

As discussed, the front shield is preferably removable. The purpose for this is to allow the shield to be removed, rotated and placed on the base 12 when sterilizing the device 10 in an autoclave. In this way the shield may be tall enough to provide shielding but not be a limiting factor when trying to put the device in an autoclave. Of course this objective may be accomplished by other means such as placing a hinge point along the height of the shield 16 so that part of the shield could be folded down when autoclaving. However, the removable shield is preferable since it will also allow the operator the option of removing the shield if desired.

The front shield 16 is also preferably movable. In the preferred embodiment, this is accomplished by snapping the shield 16 into the groove 32. In this way the shield 16 may be slid along groove 32 to the desired position.

Figure 4:
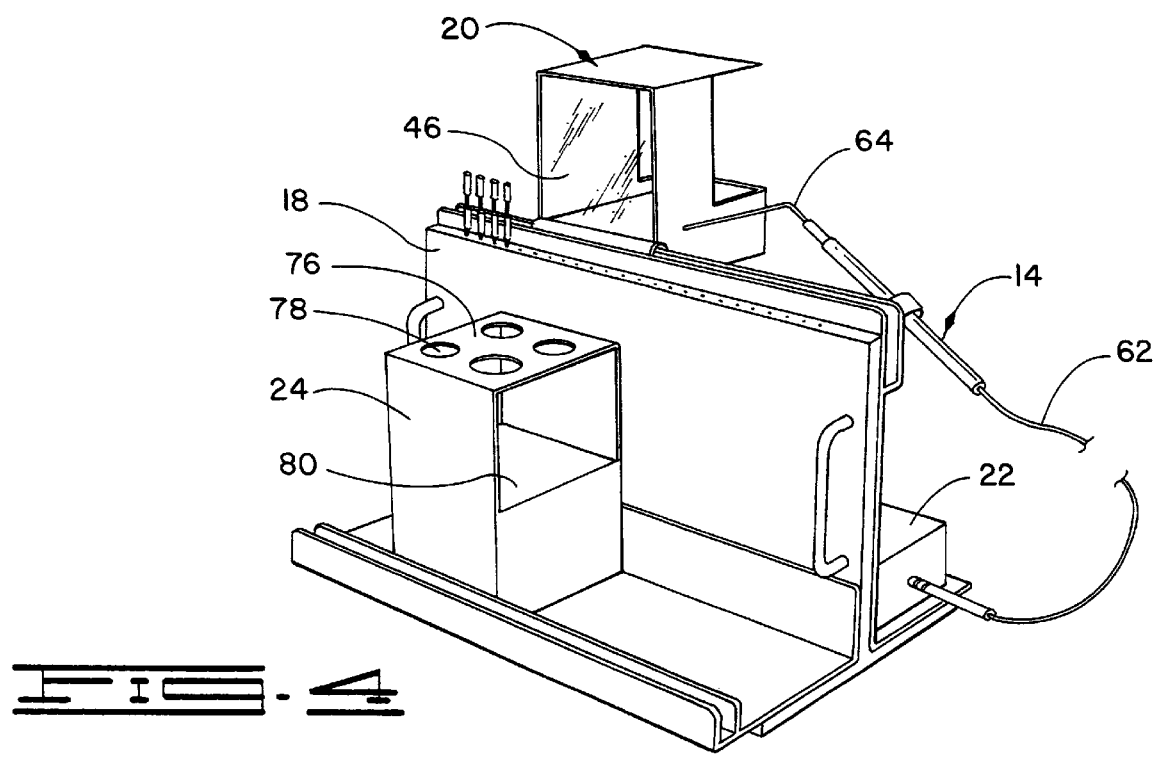
FIG. 4 is a front perspective view of a radioactive seed handling device constructed in accordance with the present invention with a front shield removed.

Referring to FIGS. 3 and 4, the shielded seed working tray 20 preferably includes a transparent front shield and a bottom 48. The seed working tray may also include raised edges such as edges 50 and 52 to hold seeds on the tray. In the most preferred embodiment, the seed working tray 20 includes additional shields such as top shield 54 and side shields 56 and 58. If side shields are included, at least a portion of at least one side shield of the tray 20 should be left open to allow the seed handling wand 14 to reach the seeds. For example, as shown in the figures, side shield 58 only extends midway back from the transparent front 46.

Referring back to FIG. 2, the Seed handling wand 14 has a handle 60. The handle 60 has a passage therein, with one end of the passage being in communication with a vacuum source tube 62 and the opposite end of the passage being in communication with a seed probe 64. An aperture 66 is provided in the handle and in communication with the passage in the handle to work as a bypass. Thus, air drawn in through the vacuum source tube will come into the handle through the aperture 66. If the aperture 66 is blocked, such as by the operator's finger, then air will be drawn through the seed probe 64.

The seed probe 64 extends from the handle 60 at an angle 68 from the axis of the handle. The angle is preferably between fifteen and seventy-five degrees and more preferably between thirty and sixty degrees, and most preferably about forty-five degrees. The seed probe may be made from two connected conduits. The first conduit 70 is connected to the handle 60 and includes the angle 68. The second conduit 72 may then be removably connected to the first conduit 70. In this way, a new conduit 72 may be connected whenever desired, such as when the old conduit is broken or a new sterile conduit 70 may be connected each time the device 10 is used.

A stop 74 should be provided in seed probe 64 to prevent seeds from being sucked up into handle 60. The stop may be placed in either the first or the second conduit, but is preferably placed generally where the first and the second conduits join. Some suitable stops include a narrowed portion in the probe or material such as mesh and fibers placed in the probe which will allow air to pass through the conduit but will stop seeds or spacers.

At least the second conduit 72 should be partially or completely transparent to allow for visual verification of the seeds and spacers loaded into the conduit. This transparency allows the operator to suck up seeds and spacers in the proper order, look at the probe 64 to verify the order and then release the seeds and spacers. Markings may be provided on the probe to aid the operator in counting seeds or spacers therein.

The bulk seed storage container 24 is provided to hold vessels such as bottles of seeds or spacers, calibration vessels and the like. Preferably, the bulk container is a shielded container having means to hold such bottles and vessels with the sides shielded but with the tops accessible. The bulk container 24 should hold the bottles and vessels elevated from the base of the device to provide easy access. In addition, the bulk container 24 should be free-standing to allow the operator to move it to a desired location, either on or off of the device. One suitable device to accommodate each of the above listed requirements is shown in FIGS. 1, 3 and 4. The shown container 24 has a shielded box with a top 76 and a bottom (not shown). A shelf 80 is placed in the box between the top 76 and the bottom. A plurality of apertures of various sizes 78 (only one aperture being labeled in the drawings) are provided in the top 76. In this way, bottles or vessels may be placed through an aperture where they are held and are not likely to be knocked over. The bottles or vessels may be supported by the shelf 80, or may hang from the sides of the aperture. In either way, the sides of the bottles or vessels are shielded by the box and the tops are accessible. One or more side areas of the container 24 may be left open and unshielded to provide means to store additional objects in the container. Thus, if one complete side is left open one could store objects below the shelf 80.

Figure 5:
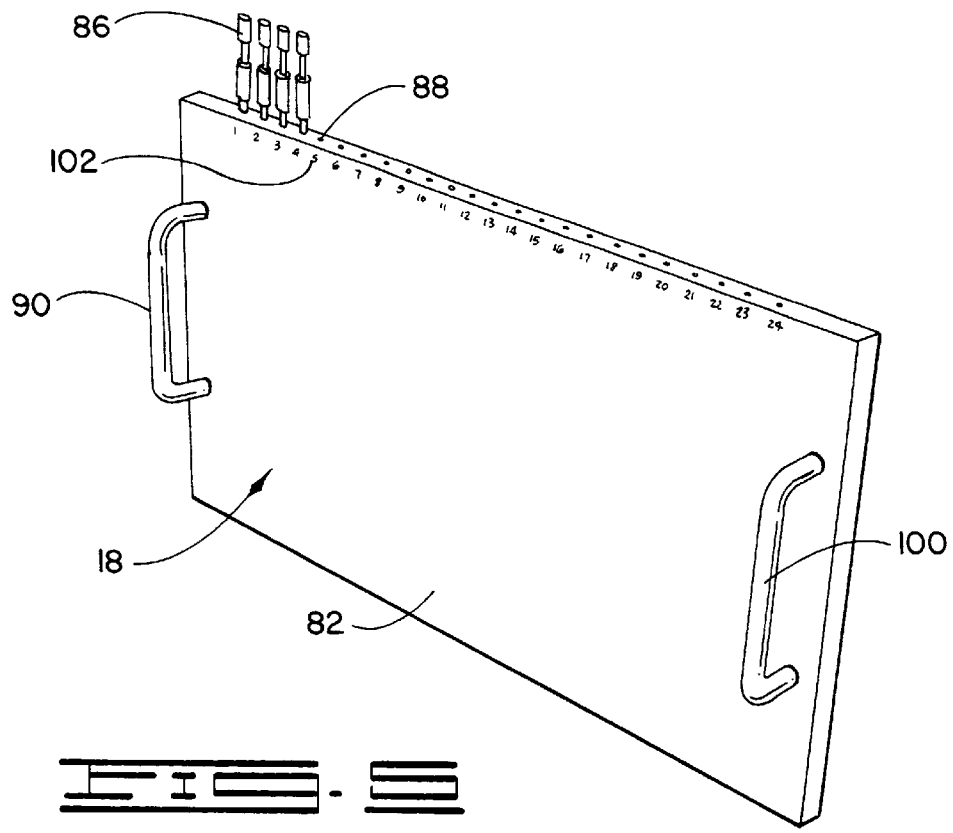
FIG. 5 is a front perspective view of a needle rack of the invention of FIG. 1.
Figure 6:
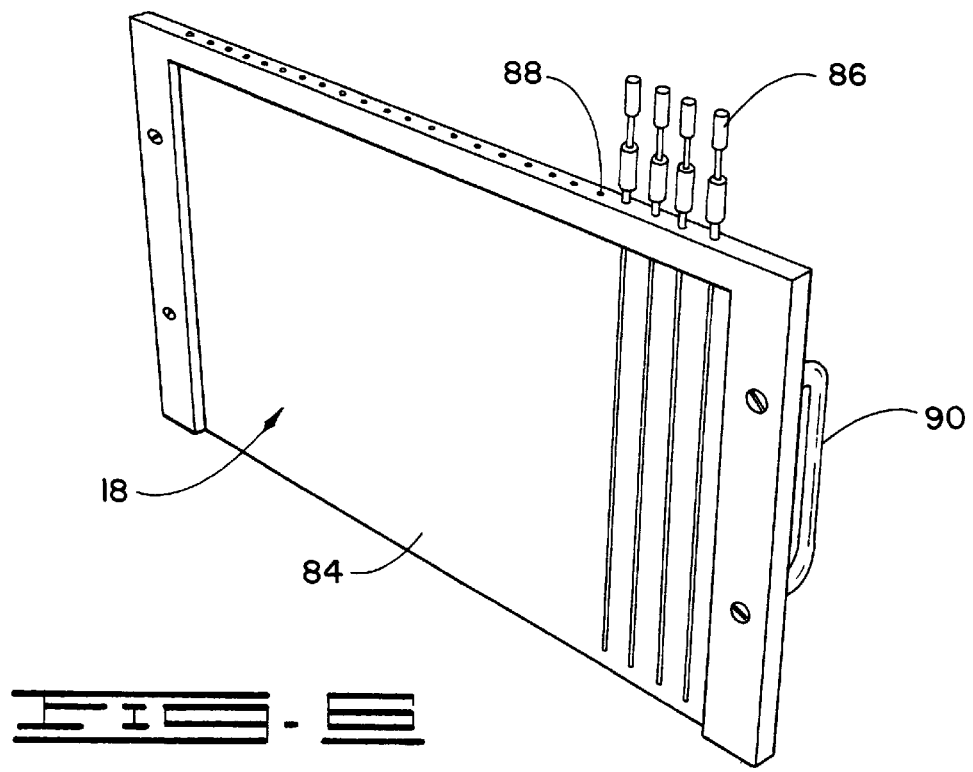
FIG. 6 is a rear perspective view of the needle rack of FIG. 5.

The needle rack 18 is removably mounted to the base 12 and provides support and shielding for a plurality of needles (such as needle 86) held generally parallel in a single plane. The needle holder has a shielded front 82 (FIG. 5) and an open recessed back 84 (FIG. 6). Thus, when the needle rack is mounted on the base 12, the needles are shielded on the front side by the needle rack front 82, and are shielded on the back side by the center divider 34. The needles are held by being placed in apertures (such as aperture 88) in the top of the needle rack. An additional holding device may be provided to hold the bottom of the needles. Suitable devices include a member which extends from side to side of the needle rack or an edge with apertures similar to the apertures on the top.

The apertures 88 may have corresponding numbers 102 to aid in keeping track of the number of needles in the rack. For example, aperture 88 is the fifth aperture from the left of the needle rack and the number five is marked near the aperture. The needle rack also includes handles 90 and 100 to provide means for moving the rack and needles to an x-ray film for verification of the number and placement of the seeds in the needles.

Figure 7:
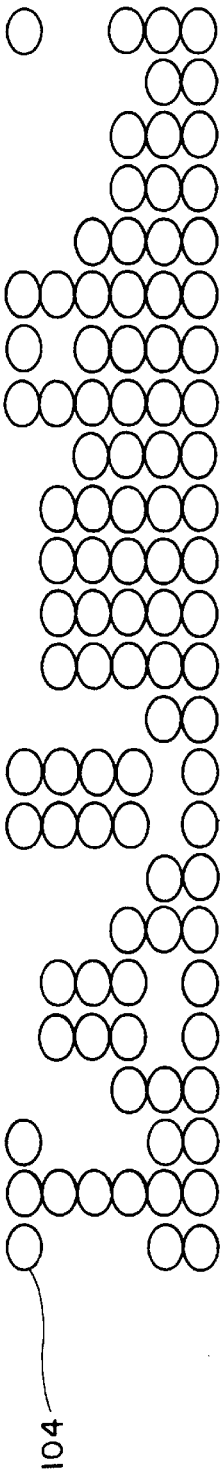
FIG. 7 is an example of an autoradiographic verification of a set of needles held in the needle rack of FIG. 6.

Referring now to FIG. 7, shown therein is an example of an x-ray film after a loaded needle holder has been use to expose the film. Each seed shows up as an exposed spot 104 on the film. Thus, in the example needle number 1 had three seeds. The exposed spot 104 is spaces apart from the remaining two spots in needle number 1; this was accomplished by spacers between the seeds. Additional information may also be placed on the film either through exposure or by writing. For example, the needle number and the number of seeds in each needle may be placed on the film.

In operation, the device 10 should be sterilized before use. This may be accomplished by removing the front shield 16 and then laying it on the base. Of course, if a foldable front shield is provided, the shield may be simply folded down. The shielded seed working tray 20 is removed and stacked on the base and the vacuum source is removed. The device 10 should now be small enough to fit in a standard autoclave.

After sterilization and cooling, the device is set up for work by replacing the front shield, the seed working tray and the vacuum source. The operator may now begin or other procedures with the device. Seeds may be picked up from the bulk seed container 24 or directly from a factory container.

To pick up seeds and/or spacers, the operator blocks the aperture 66 with a finger and then places the end of the seed probe 64 next to either end of a seed or spacer. The vacuum from vacuum tube 62 is then directed through the seed probe which sucks up the desired seed or spacer. Since the seed probe has an internal diameter somewhat larger than the external diameter of a seed or spacer, air will pass around a seed in the probe to the vacuum source. Because of this, additional seeds or spacers may be picked up without releasing seeds already in the probe. This allows the operator to pick up a string of seeds and/or spacers and then verify what has been picked up by looking through the transparent probe to verify number, type and order. Thus, if one chose to load a needle such as needle number one shown in FIG. 7, one would pick up two seeds, then three spacers and then another seed. After picking them up the operator could look at the probe to verify the proper number and order of seeds and spacers. Then the end of the probe may be placed over needle number one and the operator's finger removed from the aperture 66 in the handle 60. This will allow the seeds to drop into needle number one in the proper order.

After all the desired needles have been loaded, the operator may grasp the needle rack 18 by handles 90 and 100 and move the rack to a location for autoradiographing. Since the needle rack has a front shield 82, the operator is shielded from radiation while moving the needle rack. The needle rack 18 may then be placed on a sheet of film to expose portions of film near seeds. The resulting negative shows the number and location of seeds and spacers such as shown in FIG. 7.

Changes may be made in the combinations, operations and arrangements of the various parts and elements described herein without departing from the spirit and scope of the invention as defined in the following claims.

I claim:

1. A radioactive seed handling device comprising:

a base; and a needle rack removably attached to said base for holding a plurality of needles generally parallel in a single plane while radioactive seeds are dropped into said needles wherein the needle rack may be removed from the base and laid in a plane parallel to said single plane, and wherein the needle rack includes a front shield for shielding an operator from radiation emitted from seeds in needles in said rack.

2. The radioactive seed handling device of claim 1 further comprising:

a vacuum source; and a seed handling wand connected to said vacuum source by a conduit, said wand having a handle and a probe, said probe being connected to said handle and extending from the handle at an angle between fifteen and seventy-five degrees.

3. The seed handling device of claim 2, wherein the probe has a first and a second conduit, said first conduit being connected to the handle and said second conduit being removably connected to the first conduit.

4. The seed handling device of claim 3, wherein the second conduit is at least partially transparent to allow for visual verification of seeds in the conduit.

5. The seed handling device of claim 4, further comprising a front shield movably connected to the base and extending up therefrom, said shield having at least a portion thereof being transparent to allow an operator to remain in a shielded area and have a view to load seeds in a needle in the needle holder.

6. The radioactive seed handling device of claim 1 further comprising; a seed handling wand connected to a vacuum source, said wand having a handle and a probe, and said probe being connected to said handle and extending from the handle at an angle between fifteen and seventy-five degrees.

7. The seed handling device of claim 6, wherein the probe has a first and a second conduit, said first conduit being connected to the handle and said second conduit being removably connected to the first conduit; and wherein said second conduit is at least partially transparent to allow an operator to view articles in said second conduit.

8. A radioactive seed handling device comprising:

a base wherein the base includes a center divider with a top; and wherein a shielded seed working tray is movably connected to the center divider to allow the shielded seed working tray to extend above the top of said center divider;

a needle rack removably attached to said base for holding a plurality of needles generally parallel in a single plane while radioactive seeds are dropped into said needles, wherein the needle rack includes a front shield for shielding an operator from radiation emitted from seeds in needles in said rack;

a vacuum source;

a seed handling wand connected to said vacuum source by a conduit, said wand having a handle and a probe, said probe being connected to said handle and extending from the handle at an angle between fifteen and seventy-five degrees, wherein the probe has a first and a second conduit, said first conduit being connected to the handle and said second conduit being removably connected to the first conduit, wherein the second conduit is at least partially transparent to allow for visual verification of seeds in the conduit; and a front shield movably connected to the base and extending up therefrom, said shield having at least a portion thereof being transparent to allow an operator to remain in a shielded area and have a view to load seeds in a needle in the needle holder.

9. The seed handling device of claim 8, further comprising: movable a bulk seed storage container, said bulk seed storage container having a top with one or more apertures therein for holding vessels to allow the operator to access seeds in said vessels with said probe while working with the device.

10. A radioactive seed handling device comprising:

a base, wherein the base includes a center divider with a top; and means on said center divider generally near said top for movably connecting a seed working tray;

a needle rack removably attached to said base for holding a plurality of needles generally parallel in a single plane while radioactive seeds are dropped into said needles; and a vacuum powered wand having a handle and a probe, wherein at least a portion of said probe extends from said handle at an angle between fifteen and seventy-five degrees.

11. The radioactive seed handling device of claim 10, wherein said means for movably connecting a seed working tray comprises a groove in said center divider.

12. The radioactive seed handling device of claim 10, further comprising a front shield movably connected to said base and extending up therefrom, and wherein at least a portion of said front shield is transparent.

13. A radioactive seed handling device comprising: a base, wherein the base includes a divider with a top and means on said divider generally near said top for movably connecting a seed working tray; and a needle rack attached to said base for holding a plurality of needles.

* * * * *